US010667793B2

(12) United States Patent
Halmann et al.

(10) Patent No.: US 10,667,793 B2
(45) Date of Patent: Jun. 2, 2020

(54) METHOD AND SYSTEM FOR ENHANCED VISUALIZATION AND SELECTION OF A REPRESENTATIVE ULTRASOUND IMAGE BY AUTOMATICALLY DETECTING B LINES AND SCORING IMAGES OF AN ULTRASOUND SCAN (71) Applicant: General Electric Company, Schenectady, NY (US)

(72) Inventors: Menachem Halmann, Wauwatosa, WI (US); Alexander Sokulin, Tirat Carmel (IL); Peter Lysyansky, Tirat Hacarmel (IL); Lilach Vanuk, Tirat Hacarmel (IL); Cynthia Owen, Powhatan, AR (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 1213 days.

(21) Appl. No.: 14/869,560

(22) Filed: Sep. 29, 2015

(65) Prior Publication Data

US 2017/0086794 A1    Mar. 30, 2017

(51) Int. Cl.
*A61B 8/08* (2006.01)
*G06T 7/00* (2017.01)
*A61B 8/00* (2006.01)

(52) U.S. Cl.
CPC .......... *A61B 8/5215* (2013.01); *A61B 8/0875* (2013.01); *A61B 8/461* (2013.01);
(Continued)

(58) Field of Classification Search
CPC ....... A61B 5/0031; A61B 5/08; A61B 5/4878; A61B 8/12; A61B 8/4472; A61B 8/461;
(Continued)

(56) References Cited

U.S. PATENT DOCUMENTS 5,797,397 A * 8/1998 Rosenberg ............... A61B 8/00
                                                                                    600/400
2008/0212854 A1* 9/2008 Fukatsu ................ G06F 19/321
                                                                                    382/128
(Continued)

FOREIGN PATENT DOCUMENTS

WO      2008073560 A2     6/2008
WO      2013181300 A1    12/2013
WO      WO2014/195742 A1 * 11/2014 ............... A61B 8/00

OTHER PUBLICATIONS

Brattain, Laura J., et al., "Automated B-Line Scoring on Thoracic Sonography," American Institute of Ultrasound in Medicine, JUltrasound Med 2013; 32, pp. 2185-2190.
(Continued)

*Primary Examiner* — Elmer M Chao
(74) *Attorney, Agent, or Firm* — McAndrews, Held & Malloy, Ltd.; Jacob Groethe; David Bates (57) ABSTRACT An ultrasound device performs an ultrasound scan to acquire a video clip having a plurality of images in a selected zone of a set of lungs. The ultrasound device detects B lines in each of the images of the video clip. The ultrasound device assigns a score to each of the images of the video clip based at least in part on the detected number of B lines. The ultrasound device highlights the detected B lines in each of the images of the video clip. The ultrasound device identifies a representative image from the highlighted images of the video clip in the selected zone. The identification of the representative image is based at least in part on the assigned score of each of the images. The ultrasound device displays the identified representative image.

20 Claims, 8 Drawing Sheets (52) U.S. Cl.
CPC .......... *A61B 8/5223* (2013.01); *G06T 7/0016* (2013.01); *G06T 2207/10016* (2013.01); *G06T 2207/10132* (2013.01); *G06T 2207/30061* (2013.01)

(58) Field of Classification Search
CPC ... A61B 8/0875; A61B 8/5223; A61B 8/5215; G06T 2207/10132; G06T 2207/30061; G06T 2207/10016; G06T 7/0016
See application file for complete search history.

(56) References Cited

U.S. PATENT DOCUMENTS

| | | |
|---|---|---|
| 2009/0036777 A1* | 2/2009 | Zhang .................. A61B 5/0031 600/459 |
| 2013/0184584 A1 | 7/2013 | Berkey |
| 2014/0039313 A1 | 2/2014 | Palti |
| 2014/0233826 A1* | 8/2014 | Agaian .................. G16H 50/30 382/133 |
| 2014/0276048 A1 | 9/2014 | Kiley et al. |
| 2014/0316266 A1 | 10/2014 | Ruben et al. |
| 2015/0002538 A1 | 1/2015 | Sohn et al. |

OTHER PUBLICATIONS

Anderson, Kenton, MD, et al., "Inter-Rater Reliability of Quantifying Pleural B-Lines Using Multiple Counting Methods," American Institute of Ultrasound in Medicine, JUltrasound Med 2013; 32, pp. 115-120.

\* cited by examiner

FIG. 1

-- PRIOR ART --

-- PRIOR ART --

METHOD AND SYSTEM FOR ENHANCED VISUALIZATION AND SELECTION OF A REPRESENTATIVE ULTRASOUND IMAGE BY AUTOMATICALLY DETECTING B LINES AND SCORING IMAGES OF AN ULTRASOUND SCAN

CROSS-REFERENCE TO RELATED APPLICATIONS/INCORPORATION BY REFERENCE

[Not Applicable]

FIELD OF THE INVENTION

Certain embodiments of the invention relate to ultrasound imaging. More specifically, certain embodiments of the invention relate to a method and system for enhanced visualization and selection of a representative ultrasound image by automatically detecting B lines and scoring images of an ultrasound scan.

BACKGROUND OF THE INVENTION

Ultrasound imaging is a medical imaging technique for imaging organs and soft tissues in a human body. Ultrasound imaging uses real time, non-invasive high frequency sound waves to produce a series of two-dimensional (2D) and/or three-dimensional (3D) images.

For many years, ultrasound was not used to evaluate the lung because in normal conditions, the only detectable structure is the pleura, which appears as a hyper-echoic horizontal line moving synchronously with respiration. Later, it was found that the acoustic mismatch needed to reflect an ultrasound beam may be created when the air content in the lungs decrease, such as in patients with pulmonary edema, acute respiratory distress syndrome (ARDS), pneumonia, and pulmonary fibrosis. Specifically, the presence of extravascular lung water during an ultrasound scan causes comet-tail reverberation artifacts, called B lines, ultrasound lung comets, or lung rockets, to be visible in the ultrasound images. These B lines, which appear as bright vertical lines that extend from the pleura to the bottom of the ultrasound image, can be used to assess the severity of pulmonary edema and may also be helpful in evaluating patients with ARDS, pneumonia, and pulmonary fibrosis.

Lung functional is regional in nature. For example, a condition present in one section of one lung may not be present in other sections of the same lung or in the other lung. Moreover, analysis of lung ultrasound images is typically performed on an ultrasound scan covering at least one breathing cycle. Currently, a physician may review and analyze multiple images from multiple zones of the lungs to score the condition of each zone of the lungs based on the number of B lines identified in the images. The review, analysis, and manual scoring of the large number of images is a labor intensive process that is imprecise due to the subjective identification of B lines by different physicians.

Existing ultrasound and post-processing systems do not automatically identify a representative ultrasound image for documentation in each zone. Furthermore, existing systems do not enhance the visualization of the B lines for review of an operator of an ultrasound system. Moreover, existing systems do not facilitate the comparison of images and scores between previous and current examinations to assist with assessing improvement or deterioration of a patient condition.

Further limitations and disadvantages of conventional and traditional approaches will become apparent to one of skill in the art, through comparison of such systems with some aspects of the present invention as set forth in the remainder of the present application with reference to the drawings.

BRIEF SUMMARY OF THE INVENTION

A system and/or method is provided for enhanced visualization and selection of a representative ultrasound image by automatically detecting B lines and scoring images of an ultrasound scan, substantially as shown in and/or described in connection with at least one of the figures, as set forth more completely in the claims.

These and other advantages, aspects and novel features of the present invention, as well as details of an illustrated embodiment thereof, will be more fully understood from the following description and drawings.

DETAILED DESCRIPTION OF THE INVENTION

Certain embodiments of the invention may be found in a method and system for enhanced visualization and selection of a representative ultrasound image by automatically detecting B lines and scoring images of an ultrasound scan. For example, aspects of the present invention have the technical effect of providing optimized image acquisition parameters for detection of B lines in ultrasound images.

Moreover, aspects of the present invention have the technical effect of automatically providing real-time ultrasound images enhanced to identify B lines for presentation to an ultrasound operator. Additionally, aspects of the present invention have the technical effect of automatically identifying a representative ultrasound image for acceptance by an ultrasound operator to provide documentation of each ultrasound scan zone. Furthermore, aspects of the present invention have the technical effect of facilitating the comparison of images and scores between previous and current examinations to assist with assessing improvement or deterioration of a patient condition by automatically identifying and retrieving previous related ultrasound examination images.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized and that structural, logical and electrical changes may be made without departing from the scope of the various embodiments of the present invention. The following detailed description is, therefore, not to be taken in a limiting sense, and the scope of the present invention is defined by the appended claims and their equivalents.

As used herein, an element or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode such as B-mode, CF-mode and/or sub-modes of CF such as TVI, Angio, B-flow, BMI, BMI_Angio, and in some cases also MM, CM, PW, TVD, CW where the "image" and/or "plane" includes a single beam or multiple beams.

Furthermore, the term processor or processing unit, as used herein, refers to any type of processing unit that can carry out the required calculations needed for the invention, such as single or multi-core: CPU, Graphics Board, DSP, FPGA, ASIC or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". Also, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

Figure 1:
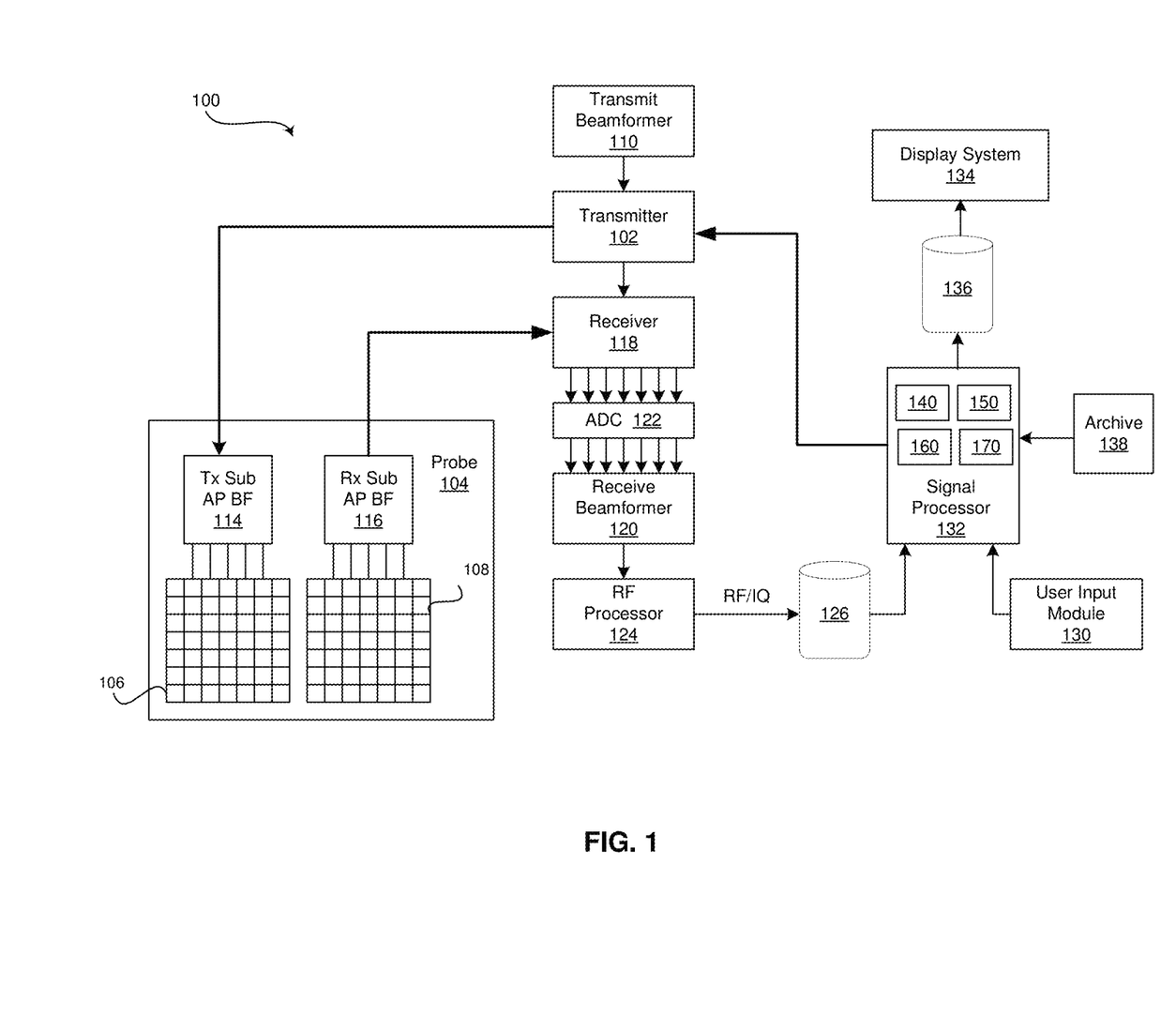
FIG. 1 is a block diagram of an exemplary ultrasound system that is operable to provide enhanced visualization and selection of a representative ultrasound image by automatically detecting B lines and scoring images of an ultrasound scan, in accordance with an embodiment of the invention.

FIG. 1 is a block diagram of an exemplary ultrasound system 100 that is operable to provide enhanced visualization and selection of a representative ultrasound image by automatically detecting B lines 206 and scoring images 300 of an ultrasound scan, in accordance with an embodiment of the invention. Referring to FIG. 1, there is shown an ultrasound system 100 comprising a transmitter 102, an ultrasound probe 104, a transmit beamformer 110, a receiver 118, a receive beamformer 120, a RF processor 124, a RF/IQ buffer 126, a user input module 130, a signal processor 132, an archive 138, an image buffer 136, and a display system 134.

The transmitter 102 may comprise suitable logic, circuitry, interfaces and/or code that may be operable to drive an ultrasound probe 104. The ultrasound probe 104 may comprise a one dimensional (1D, 1.25D, 1.5D or 1.75D) array, two dimensional (2D) array, or three dimensional (3D) array of piezoelectric elements. The ultrasound probe 104 may comprise a group of transmit transducer elements 106 and a group of receive transducer elements 108, that normally constitute the same elements.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals 107 may be back-scattered from structures in the object of interest, like blood cells or tissue, to produce echoes. The echoes are received by the receive transducer elements 108. The group of receive transducer elements 108 in the ultrasound probe 104 may be operable to convert the received echoes into analog signals, undergo sub-aperture beamforming by a receive sub-aperture beamformer 116 and are then communicated to a receiver 118.

The receiver 118 may comprise suitable logic, circuitry, interfaces and/or code that may be operable to receive and demodulate the signals from the receive sub-aperture beamformer 116. The demodulated analog signals may be communicated to one or more of the plurality of A/D converters 122. The plurality of A/D converters 122 may comprise suitable logic, circuitry, interfaces and/or code that may be operable to convert the demodulated analog signals from the receiver 118 to corresponding digital signals. The plurality of A/D converters 122 are disposed between the receiver 118 and the receive beamformer 120. Notwithstanding, the invention is not limited in this regard. Accordingly, in some embodiments of the invention, the plurality of A/D converters 122 may be integrated within the receiver 118.

The receive beamformer 120 may comprise suitable logic, circuitry, interfaces and/or code that may be operable to perform digital beamforming processing on the signals received from the plurality of A/D converters 122. The resulting processed information may be converted back to corresponding RF signals. The corresponding output RF signals that are output from the receive beamformer 120 may be communicated to the RF processor 124. In accordance with some embodiments of the invention, the receiver 118, the plurality of A/D converters 122, and the beamformer 120 may be integrated into a single beamformer, which may be digital.

The RF processor 124 may comprise suitable logic, circuitry, interfaces and/or code that may be operable to demodulate the RF signals. In accordance with an embodiment of the invention, the RF processor 124 may comprise a complex demodulator (not shown) that is operable to demodulate the RF signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces and/or code that may be operable to provide temporary storage of the RF or I/Q signal data, which is generated by the RF processor 124.

The user input module 130 may be utilized to input patient data, image acquisition and scan parameters, settings, configuration parameters, change scan mode, and the like. In an exemplary embodiment of the invention, the user input module 130 may be operable to configure, manage and/or control operation of one or more components and/or modules in the ultrasound system 100. In this regard, the user input module 130 may be operable to configure, manage and/or control operation of transmitter 102, the ultrasound probe 104, the transmit beamformer 110, the receiver 118, the receive beamformer 120, the RF processor 124, the RF/IQ buffer 126, the user input module 130, the signal processor 132, the image buffer 136, and/or the display system 134.

In various embodiments, the user input module 130 may be operable to provide image acquisition parameters. For example, a user may input parameters such as depth, gain, and focus, among other things, using the user input module 130. In an exemplary embodiment, the user input module 130 may be operable to receive a selection accepting a representative ultrasound image. For example, a user may activate a button 130 on the ultrasound probe 104 to accept and store a displayed ultrasound image 300 depicting a largest amount of B lines representing the most severe level of pulmonary edema. The user input module 130 can be a mousing device, keyboard, touch screen display, remote control, button, switch, sliding bar, voice activated input, or any suitable device or mechanism operable to receive a user input. The user input module 130 may be integrated with other components, such as the ultrasound probe 104 or display system 134, or can be a separate component.

The signal processor 132 may comprise suitable logic, circuitry, interfaces and/or code that may be operable to process the ultrasound scan data for generating an ultrasound image for presentation on a display system 134. The signal processor 132 is operable to perform one or more processing operations according to a plurality of selectable ultrasound modalities on the acquired ultrasound scan data. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In the exemplary embodiment, the signal processor 132 may comprise a parameter selection module 140, a B line processing module 150, a representative frame selection module 160, and an examination analysis module 170.

The ultrasound system 100 may be operable to continuously acquire ultrasound information at a frame rate that is suitable for the imaging situation in question. Typical frame rates range from 20-70 but may be lower or higher. The acquired ultrasound information may be displayed on the display system 134 at a display-rate that can be the same as the frame rate, or slower or faster. An image buffer 136 is included for storing processed frames of acquired ultrasound information that are not scheduled to be displayed immediately. Preferably, the image buffer 136 is of sufficient capacity to store at least several seconds worth of frames of ultrasound information. The frames of ultrasound information are stored in a manner to facilitate retrieval thereof according to its order or time of acquisition. The image buffer 136 may be embodied as any known data storage medium.

The parameter selection module 140 may comprise suitable logic, circuitry, interfaces and/or code that may be operable to import and apply image acquisition parameters to the transmitter 102 and/or transmit beamformer 110 for acquiring enhanced ultrasound image data of the target by controlling the emission of the ultrasonic transmit signals into a region of interest. The parameter selection module 140 may select the appropriate image acquisition parameters based on instructions received from a user input module 130 and/or parameters imported from an archive 138 storing previous related examination images and information. The image acquisition parameters can include depth, gain, focus, and the like. For example, B line 206 visualization in an ultrasound image 300 of the lung may be optimized by not expanding the aperture and not extending the focusing beyond a pleura 204 depth. Specifically, image processing parameters may be chosen to optimize acquisition and beamforming of the ultrasound scan to highlight the B lines 206 by setting focus delays and an aperture to a depth close to that of the pleura 204. The selection of matching image acquisition parameters by the parameter selection module 140 of the signal processor 132 for previous and current ultrasound scans of the same patient improves the reliability and consistency of B line 206 identification and scoring of the previous and current ultrasound scans. The archive 138 may be a local archive, a Picture Archiving and Communication System (PACS), or any suitable device for storing ultrasound images and related information, such as the image acquisition parameters selected for acquiring the stored ultrasound images.

Figure 2:
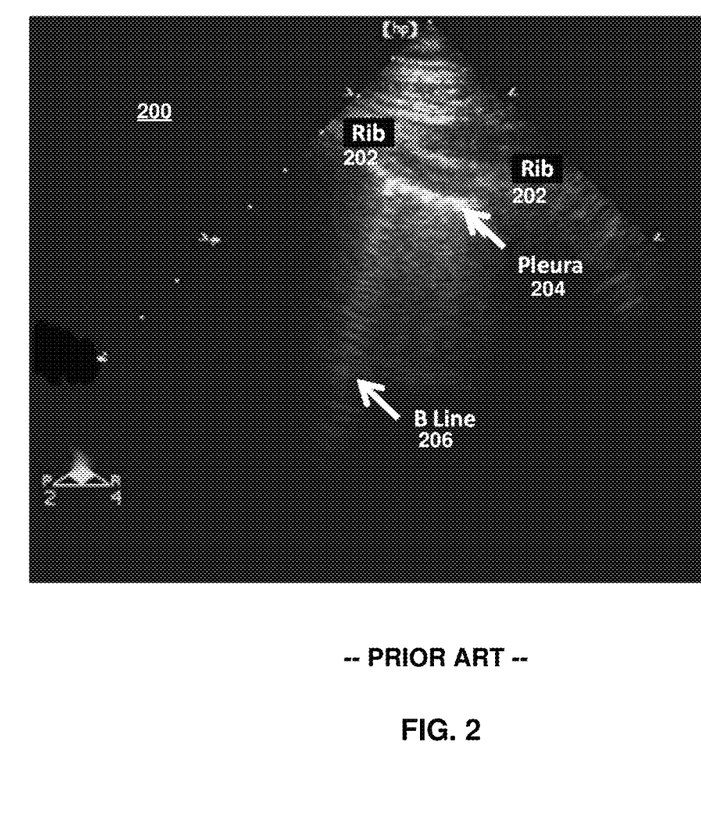
FIG. 2 is a screenshot of an exemplary ultrasound image of a portion of a lung as is known in the art.

The B line processing module 150 may comprise suitable logic, circuitry, interfaces and/or code that may be operable to identify B lines 204 in frames (also referred to as images) of an ultrasound video clip (also referred to as an ultrasound scan), enhance the visualization of the B lines 204 for presentation to an operator by highlighting 302 the B lines in each of the frames 300 of the ultrasound video clip, and score each of the ultrasound images in the video clip based on the detected B lines 204. FIG. 2 is a screenshot of an exemplary ultrasound image 200 of a portion of a lung as is known in the art. Referring to FIG. 2, an ultrasound image 200 of a lung is shown having a pleura line 204 extending generally horizontal between ribs 202, which are recognized by their acoustic shadow. A B line 206 appears as a bright vertical line that extends from the pleura 204 to the bottom of the ultrasound image 200.

Figure 3:
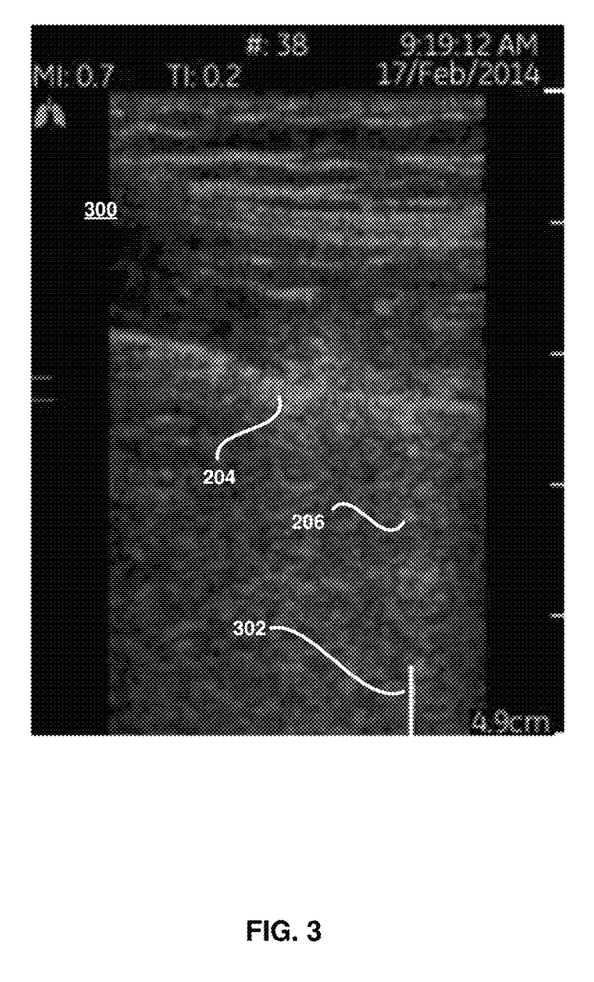
FIG. 3 is a screenshot of an exemplary enhanced ultrasound image of a portion of a lung having a marker identifying a B line, in accordance with an embodiment of the invention.

Referring again to FIG. 1, the B line processing module 150 of the signal processor 132 may apply image detection techniques and/or algorithms to automatically detect ribs 202 as superficial hyper-echoic structures with dark shadows that extend to the bottom of the image 300. In various embodiments, identification of the ribs 202 may not be necessary or possible. For example, if the ultrasound probe 104 is placed between two ribs during image acquisition, the ribs 202 may not be imaged. The B line processing module 150 may apply image detection techniques and/or algorithms to automatically detect the pleura 204 in the image 300. For example, the B line processing module 150 may search the image data for the bright horizontal section that identifies the pleura 204. In an exemplary embodiment, the pleura 204 may be identified based at least in part on the location of the detected ribs 202. The B line processing module 150 may apply image detection techniques and/or algorithms to automatically identify B lines in the image 300. For example, the B line processing module 150 may search the image data for bright vertical lines that extend from the detected pleura 204 and between identified ribs 202 to the bottom of the ultrasound image 300.

Figure 4:
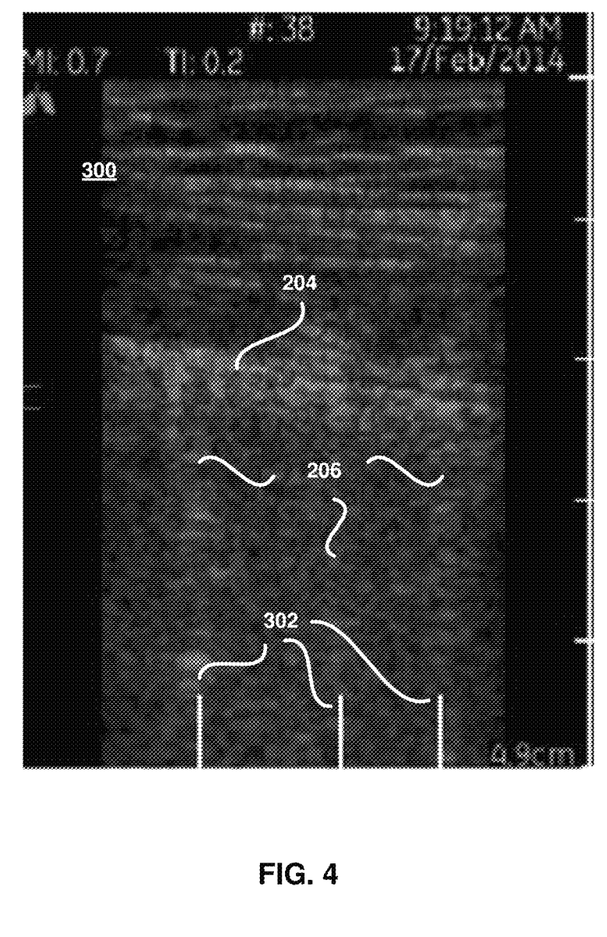
FIG. 4 is a screenshot of an exemplary enhanced ultrasound image of a portion of a lung having markers identifying B lines, in accordance with an embodiment of the invention.

In a representative embodiment, the B line processing module 150 of the signal processor 132 highlights B lines 206 in each frame 300 of an ultrasound video clip. The highlighting may be performed by superimposing a marker 302 on the image 300, colorizing the ultrasound pixels representing the B line in the image 300, and/or any suitable manner for drawing attention to detected B lines 206 for presentation to an operator and/or physician reviewing the image 300 at the display system 134. FIG. 3 is a screenshot of an exemplary enhanced ultrasound image 300 of a portion of a lung having a marker 302 identifying a B line 206, in accordance with an embodiment of the invention. FIG. 4 is a screenshot of an exemplary enhanced ultrasound image 300 of a portion of a lung having markers 302 identifying B lines 206, in accordance with an embodiment of the invention. Referring to FIGS. 3 and 4, an ultrasound image 300 of a lung is shown having a pleura line 204, one or more B lines 206, and a marker 302 identifying each B line 206. The pleura 204 appears as a generally horizontal line extending across the image 300. The one or more B lines appear as a bright vertical lines that extend from the pleura 204 to the bottom of the ultrasound image 300. In the illustrated embodiment, each B line 204 is highlighted by a vertical line marker 302 superimposed on the image 300. In various embodiments, the ultrasound images 300 having the marker(s) 302 identifying the B line(s) 206 may be dynamically presented at a display system 134 such that an operator of the ultrasound probe 104 may view the marked images 300 in substantially real-time.

Figure 6:
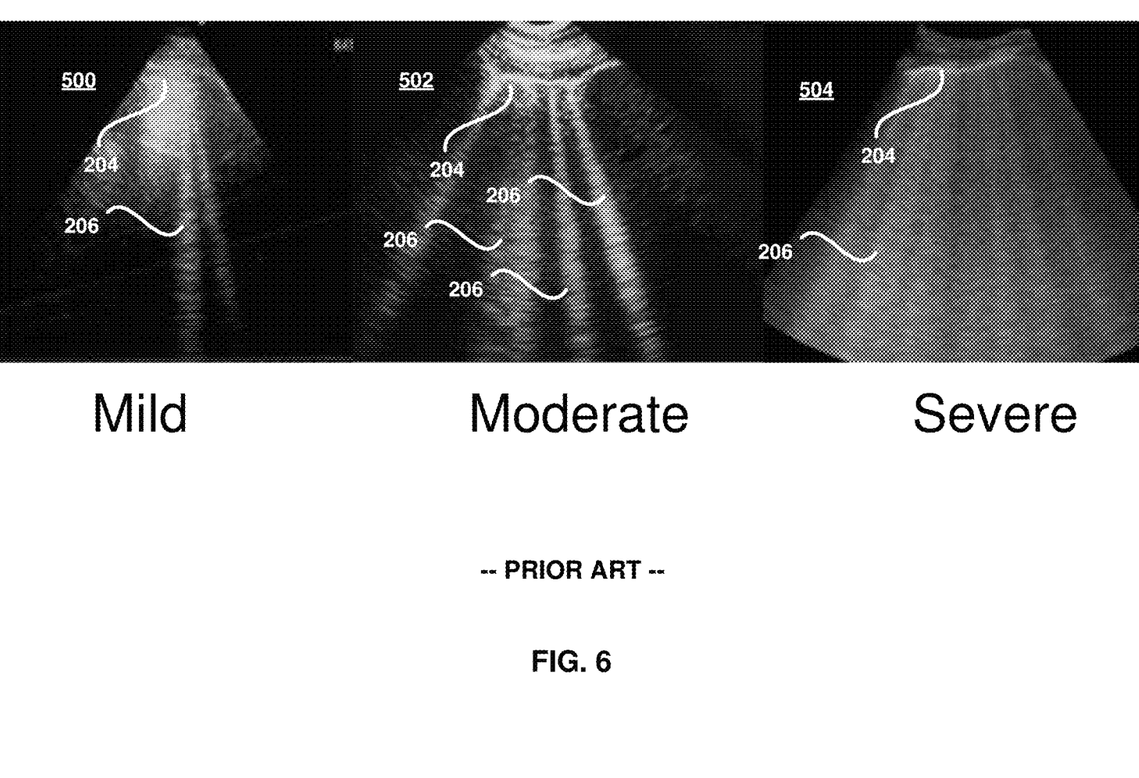
FIG. 6 is screenshots of exemplary ultrasound images of a portion of a lung having mild, moderate, and severe conditions as is known in the art.

The B line processing module 150 of the signal processor 132 scores each of the ultrasound images 300 in the video clip based at least in part on the detected B lines 204. The B line processing module 150 may apply an algorithm to count the detected number of B lines 204. The number of counted B lines 204 may be used to assign a score. The score may be a number or grade that corresponds with one of a plurality of categories. For example, 2 or less counted B lines 204 may correspond with a normal or mild condition, 3-5 B lines 204 may correspond with a moderate condition, and 6 or more B lines 204 may correspond with a severe condition. The normal or mild condition may be assigned a score or grade of 1. The moderate condition can be assigned a score or grade of 2. The severe condition may be assigned a score or grade of 3. As an example, the ultrasound image 300 of FIG. 3 having one detected B line 206 may be scored or graded at level 1 corresponding with a normal or mild condition while the ultrasound image 300 of FIG. 4 having three detected B lines 206 may be scored or graded at level 2 corresponding with a moderate condition. FIG. 6 is screenshots of exemplary ultrasound images 500, 502, 504 of a portion of a lung having mild, moderate, and severe conditions as is known in the art. Referring to FIG. 6, ultrasound images 500, 502, 504 of a lung are shown having a pleura line 204 and one or more B lines 206. The pleura 204 appears as a generally horizontal line extending across each image 500, 502, 504. The one or more B lines appear as a bright vertical lines that extend from the pleura 204 to the bottom of the ultrasound image 500, 502, 504. The mild image 500 is shown with 2 B lines 206. The moderate image 502 is shown with 5 B lines 206. The severe image 504 is shown with over 6 B lines 206. Although certain embodiments may be described in reference to exemplary counts, categories, and/or scores, unless so claimed, the scope of various aspects of the present invention should not be limited to these specific counts, categories, and/or scores and may additionally and/or alternatively be applicable to any suitable counts, categories, and/or scores. For example, more or less categories can be defined being associated with different counts of B lines 206 and corresponding with different scores or grades.

In various embodiments, the B line processing module 150 may account for a B line intensity and/or the area of converging B lines in providing a score for an ultrasound image 300. For example, referring again to FIG. 6, in some severe cases 504, B lines 206 may converge or otherwise join together. Accordingly, in addition to or instead of marking 302 each B line 206, the B line processing module 150 may mark the edges of one or more groups of joined B lines and calculate an area of the one or more groups of joined B lines to factor into a score for the ultrasound image 300. As another example, the B line processing module 150 can factor in a B line intensity when scoring the ultrasound images. The intensity and/or area scores may be used as an additional scoring mechanism and/or a tiebreaker, for example, by the representative frame selection module 160 when automatically selecting an ultrasound image depicting a most severe level of B lines as described below.

In certain embodiments, the B line processing module 150 may receive feedback from the ultrasound probe 104 and/or apply image detection and analysis techniques or algorithms to analyze the image data to check for probe 104 motion. The B line processing module 150 of the signal processor 132 may suspend scoring of the ultrasound images if the probe 104 is moving.

The representative frame selection module 160 may comprise suitable logic, circuitry, interfaces and/or code that may be operable to review each image 300 of a video clip and automatically select the image 300 with a highest score depicting a most severe level of B lines 206. For example, as an ultrasound scan is performed, the display system 134 may present the real-time image 300 enhanced with markers 302 and the automatically selected representative image 300 with markers 302. The real-time image and automatically selected representative image can be presented in separate windows, separate displays, or any suitable arrangement at the display system 134. As an example, FIG. 3 may be the real-time enhanced image 300 and FIG. 4 could be the automatically selected representative image 300 having the most severe level of B lines 206 that can correspond with the most severe level of pulmonary edema, among other things. In various embodiments, the representative frame selection module 160 may automatically select the frame 300 of the video clip having the most B lines 206. Additionally or alternatively, the representative frame selection module 160 may account for a B line intensity or area of the B lines when selecting the representative image 300. For example, the B line intensity or area of the B lines may be a tiebreaker if more than one of the frames 300 of the video clip has the same number of detected B lines 206.

After acquiring an ultrasound video clip spanning at least one breathing cycle, the operator may provide an input at the user input module 130 to accept and store the representative image 300 selected by the representative frame selection module 160. Additionally or alternatively, the operator may manually select the representative image 300 or continue to acquire ultrasound data over additional breathing cycles until a suitable representative image 300 is presented to the operator for acceptance. For example, the operator may activate a button 130 on the ultrasound probe 104 or any suitable user input module 130 to accept the representative image 300 selected by the representative frame selection module 160. The accepted frame 300 may be stored in the archive 138, which may be a local archive or PACS, for example, to document the representative image 300 selected for the particular zone of the lung.

Figure 5:
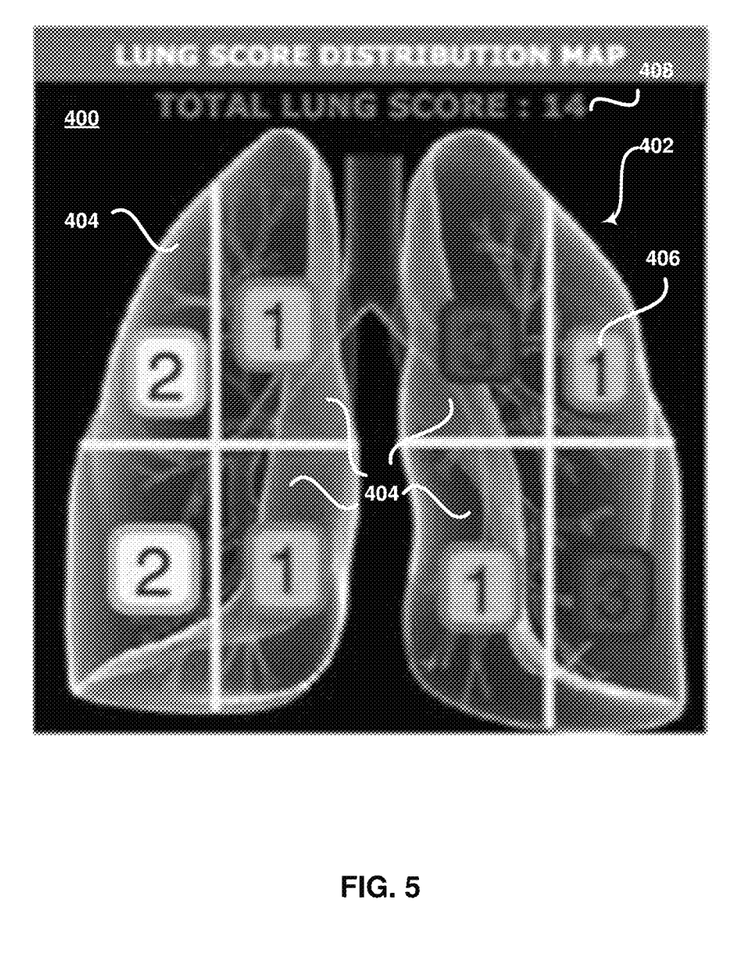
FIG. 5 is a screenshot of an exemplary user interface displaying a map of scored lung zones, in accordance with an embodiment of the invention.

The examination analysis module 170 may comprise suitable logic, circuitry, interfaces and/or code that may be operable to present current and previous examination images and tools for analyzing examination images at the display system 134. For example, the examination analysis module 170 may present a lung score distribution map 400 providing a total lung score 408 and individual scores 406 for each zone 404 of a mapped, imaged, and scored lung.

FIG. 5 is a screenshot of an exemplary user interface 400 displaying a map 402 of scored lung zones, in accordance with an embodiment of the invention. Referring to FIG. 5, the user interface 400 comprises a map layout 402 having zones 404. The zones 404 may each be assigned with a score or grade 406 based on the accepted frame 300 selected by the representative frame selection module 160. The score or grade 406 may be illustrated by the examination analysis module 170 as a letter, number, grayscale shading, color code, or any suitable mechanism for differentiating between different scores. Still referring to FIG. 5, the scores are illustrated as numbers ranging between 1 and 3 with 1 being associated with a normal or mild condition, 2 being associated with a moderate condition, and 3 being associated with a severe condition. In various embodiments, a total score 408 can also be provided by the examination analysis module 170. The total score may be a mean, medium, mode, sum, or any suitable mechanism for characterizing the condition of all of the zones 404 in the map layout 402. Referring to FIG. 5, the total score 408 is illustrated as the sum of the scores in the zones 404 of the map layout 402. In the example illustrated in FIG. 5, the total score 408 may range between 8 and 24, the lower scores being associated with normal or mild conditions and higher scores corresponding with severe conditions of the combined zones 404 in the map layout 402. The user interface 400 of FIG. 5 may be presented, for example, by the examination analysis module 170 of the signal processor 132 at the display system 134 of the ultrasound system 100.

Figure 7:
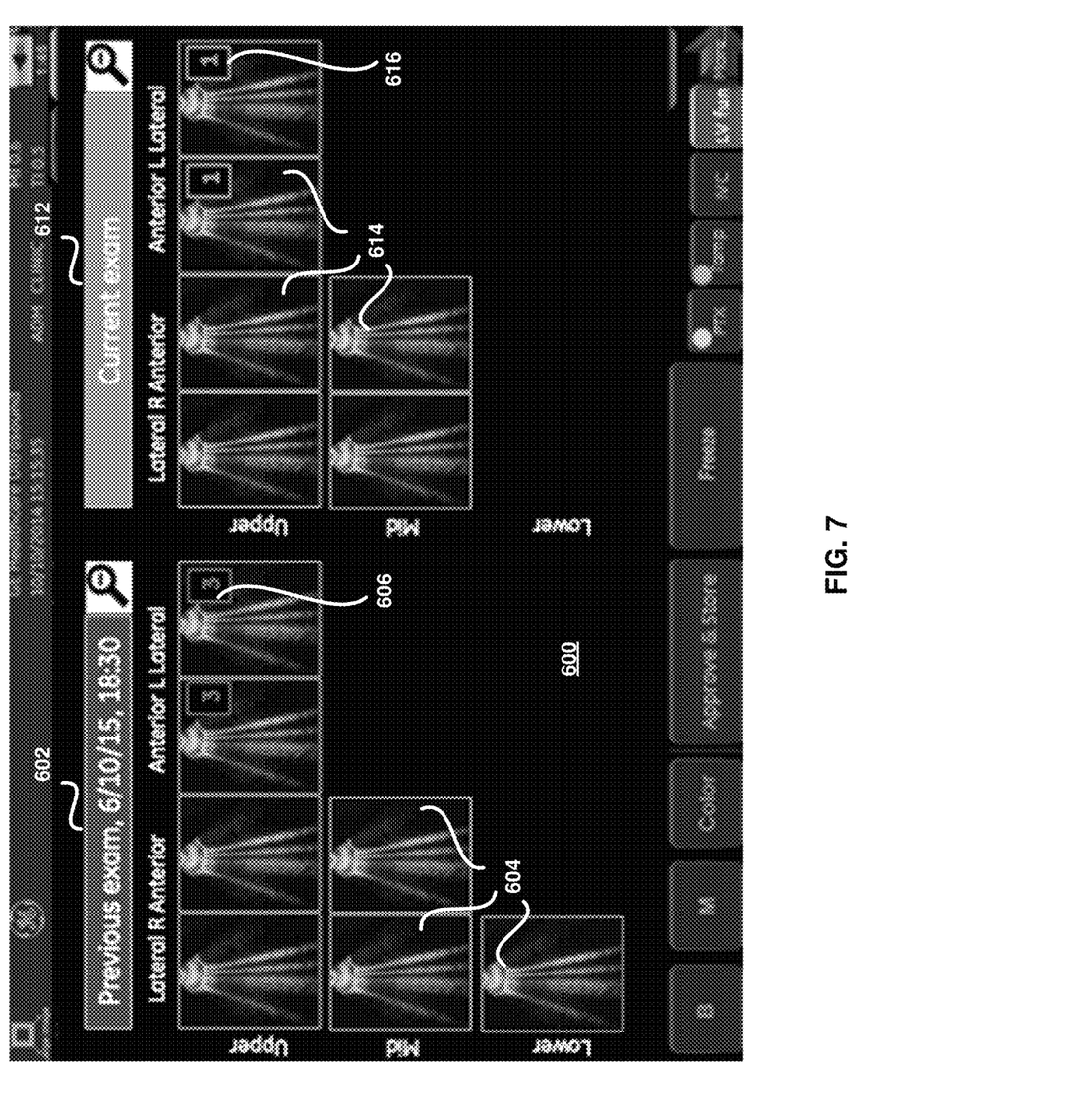
FIG. 7 is a screenshot of an exemplary user interface displaying lung ultrasound images from a current examination and a previous examination, in accordance with an embodiment of the invention.

Referring again to FIG. 1, the examination analysis module 170 may automatically retrieve previous examination images 604 from the archive 138 for comparison with current examination images 614 in an examination image user interface display 600 at the display system 134. FIG. 7 is a screenshot of an exemplary user interface 600 displaying lung ultrasound images 604, 614 from a current examination and a previous examination, in accordance with an embodiment of the invention. With reference to FIG. 7, the examination image user interface display 600 may comprise informational boxes or search boxes 602, 612 identifying sets of images 604, 614 retrieved for comparison. The images 604, 614 may be organized by zones 404 or image locations such as lower, mid, upper, right anterior, right lateral, left anterior, and left lateral, among other things. The images 604, 614, which may be the representative images 300 selected by the representative frame selection module 160 and accepted for storage by an operator, may include an indication of a score 606 that was assigned by the B line processing module 150, for example. In various embodiments, the examination analysis module 170 automatically retrieves a most recent previous examination image set 604 for comparison with a current examination image set 614. Additionally or alternatively, an operator may use search boxes 602, 612 to select examination image sets to retrieve for comparison. The images sets 604, 612 may be stored in an archive 138, such as a local archive, PACS, or any suitable storage device. The examination image user interface display 600 may be displayed at the display system 134 of the ultrasound system 100 or any suitable display component including remote display components.

Figure 8:
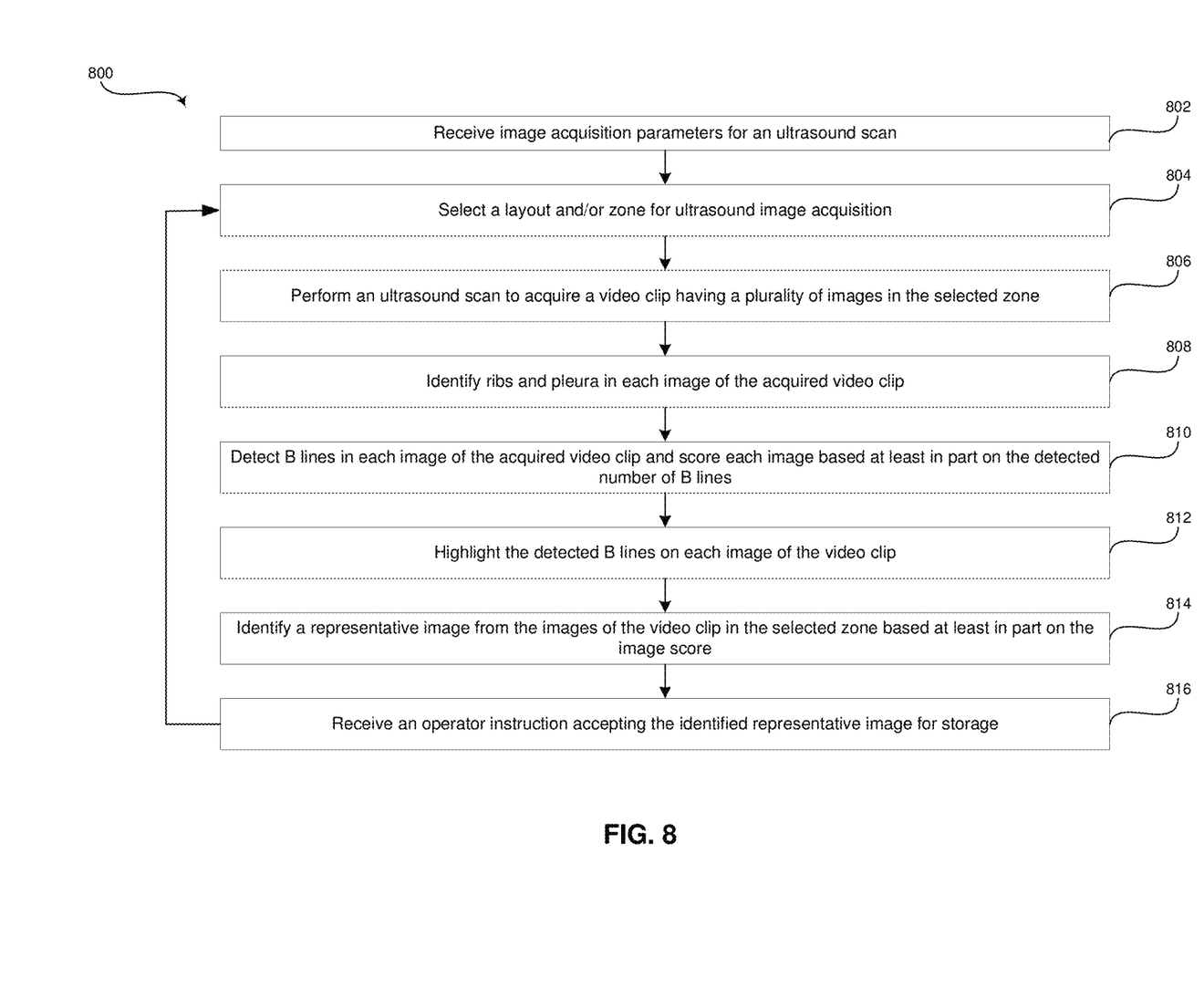
FIG. 8 is a flow chart illustrating exemplary steps that may be utilized for providing enhanced visualization and selection of a representative ultrasound image by automatically detecting B lines and scoring images of an ultrasound scan, in accordance with an embodiment of the invention.

FIG. 8 is a flow chart 800 illustrating exemplary steps 802-816 that may be utilized for providing enhanced visualization and selection of a representative ultrasound image 300 by automatically detecting B lines 206 and scoring images 300 of an ultrasound scan, in accordance with an embodiment of the invention. Referring to FIG. 8, there is shown a flow chart 800 comprising exemplary steps 802 through 816. Certain embodiments of the present invention may omit one or more of the steps, and/or perform the steps in a different order than the order listed, and/or combine certain of the steps discussed below. For example, some steps may not be performed in certain embodiments of the present invention. As a further example, certain steps may be performed in a different temporal order, including simultaneously, than listed below.

At step 802, the ultrasound system 100 may receive image acquisition parameters for an ultrasound scan. For example, the parameter selection module 140 of the signal processor 132 may retrieve image processing parameters from an archive 138. The retrieved image processing parameters may be default parameters or parameters used in a related ultrasound examination. As another example, an operator may input or adjust image processing parameters to the parameter selection module 140 via a user input module 130. The imaging processing parameters may include gain, depth, focus, and the like. The parameter selection module 140 may select or suggest image processing parameters for optimizing B line 206 visualization in the acquired ultrasound images 300, such as by choosing or suggesting image acquisition parameters that optimize acquisition and beamforming of the ultrasound scan to highlight the B lines by setting focus delays and an aperture to a depth close to that of a pleura. The image acquisition parameters selected for the ultrasound scan may be stored in the archive 138.

At step 804, an operator may select a layout 402 and/or zone 404 for ultrasound image acquisition. For example, an ultrasound scan of the lungs may be performed in multiple zones 404. The number of zones 404 and layout 402 of the zones 404 may be selected or configured by an operator. As an example, the layout 402 can have two rows and two columns at each lung for a total of eight zones 404 as illustrated in FIG. 5. The operator may also have the option to choose other layouts, such as a grid having three rows and two columns at each lung for a total of twelve zones 404, or any suitable layout 402. In various embodiments, the layout 402 may be selected or configured by the operator via a user input module 130. In certain embodiments, a default layout 402 may be automatically selected by the signal processor 132 and/or a layout 402 may be imported from an archive 138 based on a previous examination layout. Once a layout 402 is selected, an operator or a default may select a first zone 404 to image. After completing steps 806 through 816 below, the flow chart may return to step 804 to select a next zone 404 to image and continue cycling through the steps 804 through 816 of the flow chart until all zones 404 have been completed.

At step 806, the ultrasound probe 104 in the ultrasound system 100 may be operable to perform an ultrasound scan of the zone 404 selected at step 804. The ultrasound scan may result in a video clip having a plurality of frames acquired over the duration of at least one breathing cycle. The breathing cycle can be detected automatically, by a specified duration, or by an operator, among other things. For example, if a patient is using a ventilator, the ventilator can provide a signal to the signal processor 132 identifying the breathing cycle duration. As another example, the breathing cycle may be defined by an operator input at a user input module 130 or be a default value, such as 3-5 seconds. Further, an operator may identify the end of a breathing cycle by providing an input at the user input module 130, such as by pressing a button on the ultrasound probe 104.

At step 808, the B line processing module 150 of the signal processor 132 may identify ribs 202 and pleura 204 in each image 300 of the acquired video clip. For example, the B line processing module 150 of the signal processor 132 may apply image detection techniques and/or algorithms to automatically detect ribs 202 as superficial hyper-echoic structures with dark shadows that extend to the bottom of the image 300 and may search the image data for the bright horizontal section that identifies the pleura 204. In an exemplary embodiment, the pleura 204 may be identified based at least in part on the location of the detected ribs 202. In various embodiments, identification of the ribs 202 may be omitted. For example, if the ultrasound probe 104 is placed between two ribs during image acquisition, the ribs 202 may not be imaged.

At step 810, the B line processing module 150 of the signal processor 132 may detect B lines 206 in each image 300 of the acquired video clip and score each image 300 based at least in part on the detected number of B lines 206. For example, the B line processing module 150 may apply image detection techniques and/or algorithms to search the image data for bright vertical lines that extend from the detected pleura 204 and between identified ribs 202 to the bottom of the ultrasound image 300. The B line processing module 150 of the signal processor 132 scores each of the ultrasound images 300 in the video clip based at least in part on the detected B lines 204. As an example, the B line processing module 150 may apply an algorithm to count the detected number of B lines 204, which may be used to assign the score. In various embodiments, the B line processing module 150 may account for a B line intensity and/or the area of converging B lines in providing the score for an ultrasound image 300. The score may be a number or grade that corresponds with one of a plurality of categories, such as mild, moderate, and severe conditions, among other things. In certain embodiments, the B line processing module 150 may perform a check for probe 104 motion and can suspend scoring of the ultrasound images if the probe 104 is moving.

At step 812, the B line processing module 150 of the signal processor 132 may highlight the detected B lines on each image of the video clip. For example, the B line processing module 150 may highlight the detected B lines 206 by superimposing a marker 302 on the image 300, colorizing the ultrasound pixels representing the B line in the image 300, and/or any suitable manner for drawing attention to detected B lines 206 for presentation to an operator and/or physician reviewing the image 300. In various embodiments, the ultrasound images 300 having the marker(s) 302 identifying the B line(s) 206 may be dynamically presented at a display system 134 such that an operator of the ultrasound probe 104 may view the marked images 300 in substantially real-time.

At step 814, the representative frame selection module 160 may identify a representative image 300 from the images of the video clip in the selected zone 404 based at least in part on the image score. For example, the representative frame selection module 160 may be operable to review each image 300 of a video clip and automatically select the image 300 with a highest score depicting a most severe level of B lines 206. The representative frame selection module 160 may automatically select the frame 300 of the video clip having the most B lines 206. Additionally or alternatively, the representative frame selection module 160 may account for a B line intensity or area of the B lines when selecting the representative image 300. For example, the B line intensity or area of the B lines may be a tiebreaker if more than one of the frames 300 of the video clip has the same number of detected B lines 206.

At step 816, the operator may provide an instruction at the user input module 130 to accept and store the representative image 300 selected by the representative frame selection module 160. Additionally or alternatively, the operator may manually select the representative image 300 or continue to acquire ultrasound data over additional breathing cycles until a suitable representative image 300 is presented to the operator for acceptance. For example, the operator may activate a button 130 on the ultrasound probe 104 or any suitable user input module 130 to accept the representative image 300 selected by the representative frame selection module 160. The accepted frame 300 may be stored in the archive 138, which may be a local archive or PACS, for example, to document the representative image 300 selected for the particular zone of the lung. After completing step 816, the flow chart may return to step 804 to select a next zone 404 to image and continue cycling through the steps 804 through 816 of the flow chart until all zones 404 have been completed.

Upon completion of all zones 404 in the map layout 402, the examination analysis module 170 may be operable to present current and previous examination images and tools for analyzing examination images at the display system 134. For example, the examination analysis module 170 may present a lung score distribution map 400 providing a total lung score 408 and individual scores 406 for each zone 404 of a mapped, imaged, and scored lung as illustrated in FIG. 5. As another example, the examination analysis module 170 may automatically retrieve previous examination images 604 from the archive 138 for comparison with current examination images 614 in an examination image user interface display 600 at the display system 134 as illustrated in FIG. 7.

Aspects of the present invention provide a method 800 and system 100 for providing enhanced visualization and selection of a representative ultrasound image 300 by automatically detecting B lines 206 and scoring images 300 of an ultrasound scan. In accordance with various embodiments of the invention, the method 800 comprises performing 806, by an ultrasound probe 104 of an ultrasound system 100, an ultrasound scan to acquire a video clip having a plurality of images 300 in a selected zone 404 of a set of lungs. The method 800 comprises detecting 810, by a processor 132, 150 of the ultrasound system 100, B lines 206 in each of the plurality of images 300 of the video clip. The method 800 comprises assigning 810 a score 406, 616, by the processor 132, 150, to each of the plurality of images 300 of the video clip based at least in part on the detected number of B lines 206. The method 800 comprises highlighting 812, by the processor 132, 150, the detected B lines 206 in each of the plurality of images 300 of the video clip. The method 800 comprises identifying 814, by the processor 132, 160, a representative image 300, 614 from the plurality of highlighted images 300 of the video clip in the selected zone 404. The identification of the representative image 300, 614 is based at least in part on the assigned score 406, 616 of each of the plurality of images 300. The method 800 comprises displaying, by a display system 134 of the ultrasound system 100, the identified representative image 300, 614.

In a representative embodiment, the method 800 comprises receiving 816 an operator instruction, by the processor 132, 160, accepting the identified representative image 300, 614 and storing 816 the accepted representative image 300, 614 in an archive 138. In certain embodiments, the method 800 comprises automatically storing 816, by the processor 132, 160, the identified representative image 300, 614 in an archive 138. In various embodiments, acquisition and beamforming of the ultrasound scan is optimized to highlight the B lines 206 by setting focus delays and an aperture to a depth close to that of a pleura 204.

In certain embodiments, the method 800 comprises detecting 808, by the processor 132, 150, a pleura 204 in each of the plurality of images 300 of the video clip. In various embodiments, the method 800 comprises detecting 808, by the processor 132, 150, at least one rib 202 in each of the plurality of images 300 of the video clip. In a representative embodiment, the detection 808 of the pleura 204 is based at least in part on the detection 808 of the at least one rib 202.

In various embodiments, the method 800 comprises receiving a selection 804, by the processor 132, 140, of a layout 402 of the set of lungs. The layout 402 comprises a plurality of zones 404. The selected zone 404 is one of the plurality of zones 404 of the layout 402. In a representative embodiment, the method 800 is performed for each of the plurality of zones 404 of the layout 402. Each of the plurality of zones 404 of the layout 402 is associated with the accepted representative image 300, 614 to form a current examination representative image data set 612. In certain embodiments, the method comprising displaying, by the display system 134, the layout 402 comprising a representation of the assigned score 406 of the accepted representative image 300, 614 in each of the plurality of zones 404 in the layout 402. In various embodiments, the method 800 comprises retrieving, by the processor 132, 170, a prior related examination representative image data set 602 from an archive 138. The method 800 comprises displaying, by the display system 134, the current examination representative image data set 612 and the retrieved prior related examination representative image data set 602. In a representative embodiment, the highlighting in each of the plurality of images 300 of the video clip is one or more of a superimposed marker 302 corresponding with each of the detected B lines 206 and colorized pixels of the detected B lines 206.

Various embodiments provide a system comprising an ultrasound device 100 that includes an ultrasound probe 104, a processor 132, and a display system 134. The ultrasound probe 104 is operable to perform an ultrasound scan to acquire a video clip having a plurality of images 300 in a selected zone 404 of a set of lungs. The processor 132, 150 may be operable to detect B lines 204 in each of the plurality of images 300 of the video clip. The processor 132, 150 may be operable to assign a score 406, 616 to each of the plurality of images 300 of the video clip based at least in part on the detected number of B lines 206. The processor 132, 150 may be operable to highlight 302 the detected B lines 206 in each of the plurality of images 300 of the video clip. The processor 132, 160 may be operable to identify a representative image 300, 614 from the plurality of highlighted images 300 of the video clip in the selected zone 404. The identification of the representative image 300, 614 is based at least in part on the assigned score 406, 616 of each of the plurality of images 300. The display system 134 may be operable to display the identified representative image 300, 614.

In a representative embodiment, the system comprises an archive 138. The processor 132, 160 is operable to receive an operator instruction accepting the identified representative image 300, 614 and store the accepted representative image 300, 614 in the archive 138. In various embodiments, the system comprises a user input device 130 operable to provide the operator instruction to the processor 132, 160. In certain embodiments, the system comprises an archive 138. The processor 132, 160 is operable to automatically store the identified representative image 300, 614 in the archive 138. In a representative embodiment, acquisition and beamforming of the ultrasound scan is optimized to highlight the B lines 206 by setting focus delays and an aperture to a depth close to that of a pleura 204. In various embodiments, the highlighting 302 in each of the plurality of images 300 of the video clip is one or more of a superimposed marker 302 corresponding with each of the detected B lines 206 and colorized pixels of the detected B lines 206.

Certain embodiments provide a non-transitory computer readable medium having a stored thereon, a computer program having at least one code section that is executable by a machine for causing the machine to perform steps 800 disclosed herein. Exemplary steps 800 may comprise detecting 810 B lines 206 in each of a plurality of images 300 of a video clip acquired by an ultrasound scan of a selected zone 404 of a set of lungs. The steps 800 may comprise assigning 810 a score 406, 616 to each of the plurality of images 300 of the video clip based at least in part on the detected number of B lines 206. The steps 800 may comprise highlighting 812 the detected B lines 206 in each of the plurality of images 300 of the video clip. The steps 800 may comprise identifying 814 a representative image 300, 614 from the plurality of highlighted images 300 of the video clip in the selected zone 404 of the set of lungs. The identification of the representative image 300, 614 may be based at least in part on the assigned score 406, 616 of each of the plurality of images 300.

In a representative embodiment, the steps 800 may comprise the step 802 of optimizing acquisition and beamforming of the ultrasound scan to highlight the B lines 206 by setting focus delays and an aperture to a depth close to that of a pleura 204.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As an example, "x and/or y" means any element of the three-element set {(x), (y), (x, y)}. As another example, "x, y, and/or z" means any element of the seven-element set {(x), (y), (z), (x, y), (x, z), (y, z), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" to perform a function whenever the circuitry comprises the necessary hardware and code (if any is necessary) to perform the function, regardless of whether performance of the function is disabled, or not enabled, by some user-configurable setting.

Other embodiments of the invention may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for providing enhanced visualization and selection of a representative ultrasound image by automatically detecting B lines and scoring images of an ultrasound scan.

Accordingly, the present invention may be realized in hardware, software, or a combination of hardware and software. The present invention may be realized in a centralized fashion in at least one computer system, or in a distributed fashion where different elements are spread across several interconnected computer systems. Any kind of computer system or other apparatus adapted for carrying out the methods described herein is suited. A typical combination of hardware and software may be a general-purpose computer system with a computer program that, when being loaded and executed, controls the computer system such that it carries out the methods described herein.

The present invention may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present invention has been described with reference to certain embodiments, it will be understood by those skilled in the art that various changes may be made and equivalents may be substituted without departing from the scope of the present invention. In addition, many modifications may be made to adapt a particular situation or material to the teachings of the present invention without departing from its scope. Therefore, it is intended that the present invention not be limited to the particular embodiment disclosed, but that the present invention will include all embodiments falling within the scope of the appended claims.

What is claimed is:

1. A method, comprising:
performing, by an ultrasound probe of an ultrasound system, an ultrasound scan to acquire a video clip having a plurality of images in a selected zone of a set of lungs;
detecting, by a processor of the ultrasound system, B lines in each of the plurality of images of the video clip;
assigning a score, by the processor, to each of the plurality of images of the video clip based at least in part on the detected number of B lines;
highlighting, by the processor, the detected B lines in each of the plurality of images of the video clip;
identifying, by the processor, a representative image from the plurality of highlighted images of the video clip in the selected zone, the identification of the representative image based at least in part on the assigned score of each of the plurality of images; and
displaying, by a display system of the ultrasound system, the identified representative image.

2. The method according to claim 1, comprising:
receiving an operator instruction, by the processor, accepting the identified representative image; and
storing the accepted representative image in an archive.

3. The method according to claim 1, comprising automatically storing, by the processor, the identified representative image in an archive.

4. The method according to claim 1, wherein acquisition and beamforming of the ultrasound scan is optimized to highlight the B lines by setting focus delays and an aperture to a depth close to that of a pleura.

5. The method according to claim 1, comprising detecting, by the processor, a pleura in each of the plurality of images of the video clip.

6. The method according to claim 5, comprising detecting, by the processor, at least one rib in each of the plurality of images of the video clip.

7. The method according to claim 6, wherein the detection of the pleura is based at least in part on the detection of the at least one rib.

8. The method according to claim 1, comprising receiving a selection, by the processor, of a layout of the set of lungs, wherein the layout comprises a plurality of zones, and wherein the selected zone is one of the plurality of zones of the layout.

9. The method according to claim 8, comprising performing the method of claim 1 for each of the plurality of zones of the layout, wherein each of the plurality of zones of the layout is associated with the accepted representative image to form a current examination representative image data set.

10. The method according to claim 9, comprising displaying, by the display system, the layout comprising a representation of the assigned score of the accepted representative image in each of the plurality of zones in the layout.

11. The method according to claim 9, comprising:
retrieving, by the processor, a prior related examination representative image data set from an archive, and
displaying, by the display system, the current examination representative image data set and the retrieved prior related examination representative image data set.

12. The method according to claim 1, wherein the highlighting in each of the plurality of images of the video clip is one or more of:
a superimposed marker corresponding with each of the detected B lines, and
colorized pixels of the detected B lines.

13. A system, comprising:
an ultrasound device comprising:
an ultrasound probe operable to perform an ultrasound scan to acquire a video clip having a plurality of images in a selected zone of a set of lungs;
a processor operable to:
detect B lines in each of the plurality of images of the video clip,
assign a score to each of the plurality of images of the video clip based at least in part on the detected number of B lines,
highlight the detected B lines in each of the plurality of images of the video clip, and
identify a representative image from the plurality of highlighted images of the video clip in the selected zone, the identification of the representative image based at least in part on the assigned score of each of the plurality of images; and
a display system operable to display the identified representative image.

14. The system according to claim 13, comprising an archive, wherein the processor is operable to:
receive an operator instruction accepting the identified representative image, and
store the accepted representative image in the archive.

15. The system according to claim 14, comprising a user input device operable to provide the operator instruction to the processor.

16. The system according to claim 13, comprising an archive, wherein the processor is operable to automatically store the identified representative image in the archive.

17. The system according to claim 13, wherein acquisition and beamforming of the ultrasound scan is optimized to highlight the B lines by setting focus delays and an aperture to a depth close to that of a pleura.

18. The system according to claim 13, wherein the highlighting in each of the plurality of images of the video clip is one or more of:
a superimposed marker corresponding with each of the detected B lines, and
colorized pixels of the detected B lines.

19. A non-transitory computer readable medium having stored thereon, a computer program having at least one code section, the at least one code section being executable by a machine for causing the machine to perform steps comprising:
detecting B lines in each of a plurality of images of a video clip acquired by an ultrasound scan of a selected zone of a set of lungs;
assigning a score to each of the plurality of images of the video clip based at least in part on the detected number of B lines;
highlighting the detected B lines in each of the plurality of images of the video clip; and
identifying a representative image from the plurality of highlighted images of the video clip in the selected zone of the set of lungs, the identification of the representative image based at least in part on the assigned score of each of the plurality of images.

20. The non-transitory computer readable medium according to claim 19, comprising the step of optimizing acquisition and beamforming of the ultrasound scan to highlight the B lines by setting focus delays and an aperture to a depth close to that of a pleura.

* * * * *